United States Patent
Commons

(10) Patent No.: US 6,566,375 B1
(45) Date of Patent: May 20, 2003

(54) ELEVATION OF HDL CHOLESTEROL BY 4-[(AMINOTHIOXOMETHYL)-HYDRAZONO]-N-(SUBSTITUTED)-4-ARYLBUTANAMIDES

(75) Inventor: Thomas J. Commons, Wayne, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/843,308

(22) Filed: Apr. 26, 2001

Related U.S. Application Data

(62) Division of application No. 09/193,026, filed on Nov. 16, 1998.
(60) Provisional application No. 60/108,159, filed on Nov. 17, 1997, now abandoned.

(51) Int. Cl.[7] ............... H61K 31/40; H61K 31/445; C07D 211/26; C07D 211/70; C07C 337/00
(52) U.S. Cl. ............... 514/316; 514/318; 514/326; 514/330; 514/336; 514/344; 514/345; 514/354; 514/422; 514/423; 514/445; 514/447; 514/471; 514/582; 514/583; 546/297.7; 546/280.4; 546/281.4; 546/281.7; 546/284.4; 546/284.7; 546/328; 546/246; 548/517; 548/527; 548/541; 549/61; 549/62; 549/65; 549/66; 549/68; 549/71; 549/73; 549/76; 549/77; 549/474; 549/475; 549/481; 549/484; 549/496; 564/18; 564/21; 564/36
(58) Field of Search ............... 546/246, 328, 546/279.7, 280.4, 281.4, 281.7, 284.4, 284.7; 564/18, 36, 21; 549/76, 496, 61, 62, 65, 66, 68, 71, 73, 77, 474, 475, 481, 484; 548/540, 517, 527; 514/422, 423, 330, 354, 471, 316, 318, 326, 336, 344, 345, 445, 447, 582, 583

(56) References Cited

U.S. PATENT DOCUMENTS 3,826,841 A 7/1974 Yamamoto et al. ......... 424/323
5,608,109 A * 3/1997 Takagi et al. ............... 564/36

OTHER PUBLICATIONS

Vega et al., *Current Opinion in Lipidology*, 7:209–216 (1996).
Barr et al., *Am. J. Med.*, 11:480–493 (1951).
Gofman et al., *Circulation*, 34:679–697 (1966).
Picardo et al., *Arteriosclerosis.*, 6:434–441 (1986).
Glomset, *J. Lipid Res.*, 9:155–167 (1968).
Gordon et al., *Circulation*, 79:8–15 (1989).
Stampfer et al., *N. England J. Med.*, 325–381 (1991).
Badimon et al., *Lab. Invest.*, 60:455–461 (1989).
Lagocki and Scanu., *J. Biol. Chem.*, 255:3701–3706 (1978).
Schaefer et al., *J. Lipid Res.*, 23: 1259–1273 (1982).
Glass et al., *Circulation*, vol. 66, Suppl. II 102 (1982).
Miller and Miller, *Lancet*, 1:16–19 (1975).
Miller et al., *Br. Med. J.*, 282:1741–1744 (1981).
MacKinnon et al., *J. Biol. Chem.*, 261:2548–2552 (1986).
Grow and Fried, *J. Biol. Chem.*, 253:8034–8041 (1978).

* cited by examiner

Primary Examiner—Alan L. Rotman
Assistant Examiner—Raymond Covington
(74) Attorney, Agent, or Firm—Michael R. Nagy

(57) ABSTRACT

Compounds of this invention increase plasma levels of high density lipoprotein or HDL, the "good" cholesterol and as such may be useful for treating diseases such as atherosclerosis. These compounds are represented by the formula

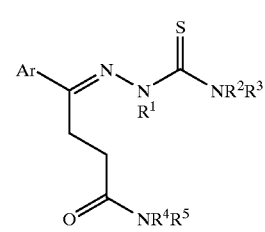

A wherein:
$R^1$, $R^2$, and $R^3$ are independently hydrogen, $C_1$–$C_6$ alkyl, phenyl or —$(CH_2)_{1-6}$ phenyl where phenyl is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_{10}$ alkyl, $C_3$–$C_8$ cycloalkyl, —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH, or $R^4$ and $R^5$ together with the nitrogen to which $R^4$ and $R^5$ are attached form a ring containing 4–7 carbon atoms;

and Ar is phenyl, naphthyl, furanyl, pyridinyl or thienyl which may be optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH.

4 Claims, No Drawings

ELEVATION OF HDL CHOLESTEROL BY 4-[(AMINOTHIOXOMETHYL)-HYDRAZONO]-N-(SUBSTITUTED)-4-ARYLBUTANAMIDES

CROSS REFERENCE TO RELATED APPLICATIONS

This application is a division of Ser. No. 09/193,026 filed Nov. 16, 1998 now, U.S. Pat. No. 6,316,467, which claims the benefit of U.S. Provisional Application No. 60/108,159, which was converted from U.S. patent application Ser. No. 08/972,119, filed Nov. 17, 1997, pursuant to a petition filed under 37 C.F.R. 153(c)(2)(i) filed Mar. 19, 1998.

FIELD OF INVENTION

This invention relates to compounds useful in elevating high density lipoprotein, the "good" cholesterol. Compounds of this invention increase plasma levels of HDL in a cholesterol fed rat model and as such these compounds may be useful for treating diseases such as atherosclerosis.

BACKGROUND OF THE INVENTION

It is widely beleived that HDL is a "protective" lipoprotein [Gloria Lena Vega and Scott Grundy, Current Opinion in Lipidology, 7, 209–216 (1996)] and that increasing plasma levels of HDL may offer a direct protection against the development of atherosclerosis. Numerous studies have demonstrated that both the risk of coronary heart disease (CHD) in humans and the severity of experimental atherosclerosis in animals are inversely correlated with serum HDL cholesterol (HDL-C) concentrations (Russ et al., *Am. J. Med.*, 11 (1951) 480–493; Gofman et al, *Circulation*, 34 (1966) 679–697; Miller and Miller, *Lancet*, 1 (1975) 16–19; Gordon et al., *Circulation*, 79 (1989) 8–15; Stampfer et al., *N. Engl. J. Med.*, 325 (1991) 373–381; Badimon et al., *Lab. Invest.*, 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles in humans appears to be correlated to a decreased number of sites of stenosis in the coronary arteries of humans (Miller et al., *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al., *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al., *Circulation*, 66 (Suppl. II) (1982) 102; MacKinnon et al., *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 8034–8041; Lagocki and Scanu, *J. Biol. Chem.*, 255 (1980) 3701–3706; Schaefer et al., *J. Lipid Res.*, 23 (1982) 1259–1273). Accordingly, agents which increase HDL cholesterol concentrations are useful as antiatherosclerotic agents, particularly in the treatment of dyslipoproteinemias and coronary artery disease.

Takagi et al., U.S. Pat. No. 5,608,109, discloses agricultural and horticultural insecticidal compounds according to formula A below where Ar and $R^2$ is optionally substituted phenyl, $R^1$ and $R^3$ are independently hydrogen, alkyl, alkenyl or alkynyl, and $R^4$ and $R^5$ are independently hydrogen or alkyl.

BRIEF DESCRIPTION OF THE INVENTION

The compounds of this invention which elevate plasma levels of HDL cholesterol have the general structure A

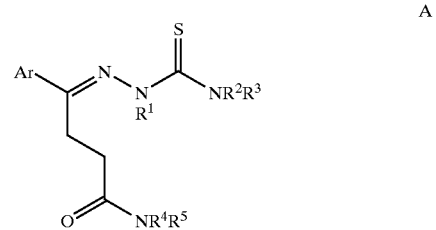

wherein:

$R^1$, $R^2$, and $R^3$ are independently hydrogen, $C_1$–$C_6$ alkyl, phenyl or —$(CH_2)_{1-6}$ phenyl where phenyl is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_{10}$ alkyl, $C_3$–$C_8$ cycloalkyl, —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH, or $R^4$ and $R^5$ together with the nitrogen to which $R^4$ and $R^5$ are attached form a ring containing 4–7 carbon atoms;

and Ar is phenyl, naphthyl, furanyl, pyridinyl or thienyl which may be optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH; with the proviso that Ar and $R^2$ cannot simultaneously be optionally substituted phenyl when the $R^1$ and $R^3$ are independently hydrogen or alkyl.

The compounds are tested in vivo in rats fed cholesterol-augmented rodent chow for 8 days according to the test protocol and blood from the rats analyzed for HDL cholesterol.

DETAILED DESCRIPTION OF THE INVENTION

The compounds of this invention are prepared by reacting 4-oxo-4-arylbutyric acid amides with an appropriately substituted thiosemicarbazide according to Scheme I. The intermediate 4-oxo-4-arylbutyric acid amides are conveniently prepared by the routes shown in Scheme II by reacting an amine of the formula $HNR^4R^5$ with either a 4-aryl-4-oxobutyric acid or a γ-aryl-γ-butyrolactone. Specific examples are given in the Experimental Section.

Scheme I: Preparation of Title Compounds

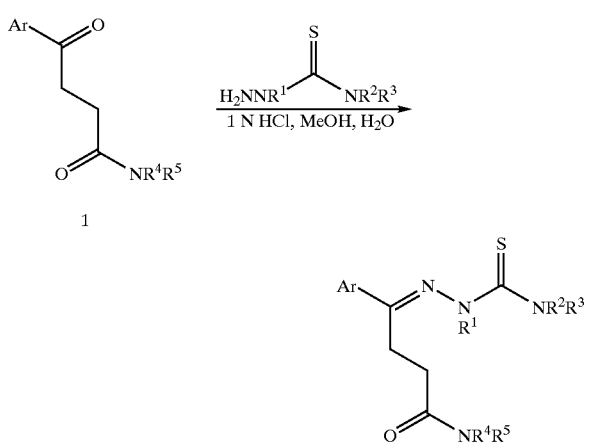

Scheme II: Preparation of Intermediate 4-oxo-4-phenylbutyric Acid Amides
(1) Route A to Ketoamide 1

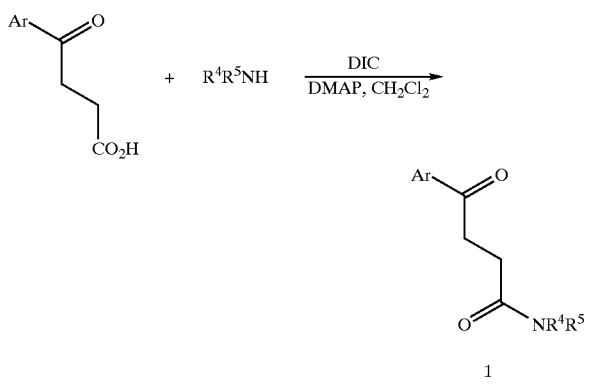

(2) Route B to Ketoamide 1

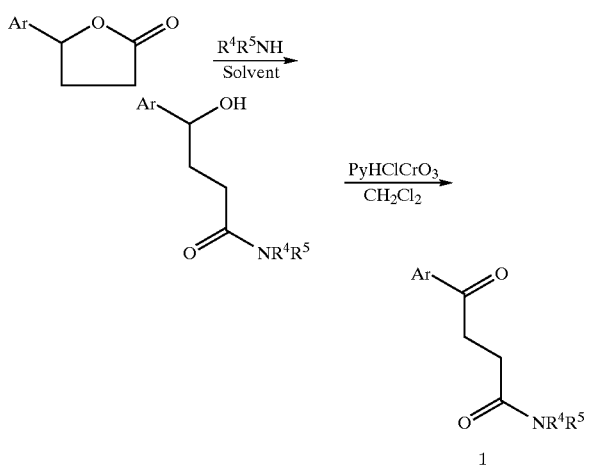

The following examples are included for illustrative purposes only and are not to be construed as limiting to this disclosure in any way. Those skilled in the art of synthetic organic chemistry may be aware of other methods of preparing compounds of this invention. The starting materials or intermediates are available commercially or can be prepared by following standard literature procedures.

EXAMPLE 1

2-(4-Butylamino-4-oxo-1-phenyl-butylidene)-hydrazinothiocarboxamide (A) 1,3-Diisopropylcarbodiimide (22.0 ml, 0.14 moles) in 200 ml of methylene chloride was added under nitrogen dropwise over 45 minutes to a solution of 3-benzoylpropionic acid (25.00 g, 0.14 moles), 4-dimethylaminopyridine (17.16 g, 0.14 moles) and butylamine (13.9 ml, 0.14 moles) in 500 ml of methylene chloride at ice bath temperature. After the addition the reaction was stirred at ice bath temperature for 1 hour. The ice bath was removed and the reaction stirred for 18 hours. The solid present was removed by filtration and discarded. The filtrate was extracted with 1 N HCl, 5% NaHCO$_3$, dried (MgSO$_4$) and the solvent removed under reduced pressure to give 35.84 g of a yellow solid. Recrystallization of the solid from isopropyl alcohol gave N-butyl-4-oxo-4-phenyl-butyramide (15.99 g, 49%) as a light yellow solid, mp 78–80° C.

Elemental Analysis for $C_{14}H_{19}NO_2$
Calc'd: C, 72.07; H, 8.21; N, 6.00.
Found: C, 72.42;, H, 8.20; N, 6.07.

(B) Thiosemicarbazide (1.95 g, 21.4 mmol) was added to a solution of N-butyl-4-oxo-4-phenyl-butyramide (5.0 g, 21.4 mmol), prepared in the previous step, in 75 ml of methanol plus 5.8 ml of 1 N HCl plus 5.8 ml of water and the reaction stirred at room temperature for 22 hours. The reaction was concentrated under reduced pressure at which time a solid formed. The solid was collected by filtration and dried to give 4.49 g of an off-white solid. Recrystallization of the solid from isopropyl alcohol gave 3.16 g (48%) of the title compound as a white solid, mp 64–68° C.

Elemental Analysis for $C_{15}H_{22}N_4OS.0.8\ C_3H_8O$
Calc'd: C, 58.95; H, 8.07; N, 15.80.
Found: C, 58.93; H, 8.25; N, 15.45.

EXAMPLE 2

4-[(Aminothioxomethyl)hydrazono]-N-(1-methylethyl)-4-phenyl-butanamide (A) In the same manner as described in step (A) of Example 1, and replacing butylamine with isopropylamine, N-(1-methylethyl)-4-oxo-4-phenyl-butyramide (10.24 g, 33%) was obtained as a white solid, trip 118–121° C.

Elemental Analysis for $C_{13}H_{17}NO_2$
Calc'd: C, 71.21; H, 7.81; N, 6.39.
Found: C, 71.14; H, 7.83; N, 6.36.

(B) Thiosemicarbazide (2.08 g, 22.8 mmol) was added to a solution of N-(1-methylethyl)-4-oxo-4-phenyl-butyramide (5.0 g, 22.8 mmol), prepared in the previous step, in 80 ml of methanol plus 6.2 ml of 1 N HCl plus 6.2 ml of water and the reaction stirred at room temperature for 2 days. An additional 1.04 g (11.4 mmol) of thiosemicarbazide was added and the reaction stirred at room temperature for 24 hours. The reaction was cooled in an ice bath and a white solid precipitated. The solid was collected by filtration and dried. Recrystallization of the solid from isopropyl alcohol gave the title compound (4.73 g, 53%) as a white solid, mp 66–71° C.

Elemental Analysis for $C_{14}H_{20}N_4OS.1.6\ C_3H_8O$
Calc'd: C, 58.12; H, 8.51; N, 14.42.
Found: C, 57.06; H, 8.58; N, 13.80.

EXAMPLE 3

4-[(Aminothioxomethyl)-hydrazono]-4-phenylbutanamide (A) A mixture of γ-phenyl-γ-butyrolactone (10.30 g, 63.5 mmol) and an excess of ammonia was stirred under nitrogen and a dry ice trap for 8 hours. The dry ice trap was removed and after evaporation of the ammonia 11.27 g of a tan solid remained. Recrystallization of the solid from ethyl acetate-hexane gave 4-hydroxy-4-phenyl-butyramide (8.56 g, 75%) as a white solid, mp 85–87° C.

Elemental Analysis for $C_{10}H_{13}NO_2$

Calc'd: C, 67.02; H, 7.31; N, 7.82.

Found: C, 67.27; H, 7.25; N, 7.84.

(B) A mixture of 4-hydroxy-4-phenyl-butyramide (4.02 g, 22.4 mmol), prepared in the previous step, and pyridinium chlorochromate (7.26 g, 33.7 mmol) in 500 ml of methylene chloride was stirred at room temperature for 2 hours. The reaction was poured onto 400 g of silica gel (230–400 mesh) and the material eluted with ethyl acetate. Isolation of the major component gave 1.92 g of a purple solid. Recrystallization of the solid from ethyl acetate gave 4-oxo-4-phenyl-butyramide (1.24 g, 31%) as a green solid, mp 122–124° C.

Elemental Analysis for $C_{10}H_{11}NO_2$

Calc'd: C, 67.78; H, 6.26; N, 7.90.

Found: C, 67.34; H, 6.15; N, 7.75.

(C) Thiosemicarbazide (1.38 g, 15.1 mmol) was added to a solution of 4-oxo4-phenyl-butyramide (1.63 g, 9.22 mmol), prepared in the previous step, in 50 ml of methanol plus 2.5 ml of 1 N HCl plus 2.5 ml of water and the reaction stirred at room temperature for 28 hours. The solid formed was collected by filtration and dried to give 1.73 g of a purple solid. Recrystallization of the solid from methanol gave the title compound (1.34 g, 58%) as a purple solid, mp 186–188° C.

Elemental Analysis for $C_{11}H_{14}N_4OS$

Calc'd: C, 52.78; H, 5.64; N, 22.38.

Found: C, 52.75; H, 5.66; N, 22.41.

EXAMPLE 4

4-[(Aminothioxomtethyl)-hydrazono]-N-benzyl-4-phenylbutanamide (A) A solution of γ-phenyl-γ-butyrolactone (5.17 g, 31.8 mmol) and benzylamine (3.48 ml, 31.8 mmol) in 200 ml of benzene was refluxed under a nitrogen atmosphere for 20 hours. An additional 1.75 ml (16.0 mmol) of benzylamine was added and the solution refluxed for 24 hours. When the reaction was partitioned with 1 N HCl a white solid precipitated. The solid was collected by filtration and dried to give N-benzyl-4-hydroxy-4-phenyl-butyramide (6.12 g, 72%) as a white solid, mp 92–94° C.

Elemental Analysis for $C_{17}H_{19}NO_2$

Calc'd: C, 75.81; H, 7.11; N, 5.20.

Found: C, 75.64; H, 7.08; N, 5.08.

(B) A mixture of N-benzyl-4-hydroxy-4-phenyl-butyramide (5.58 g, 20.7 mmol), prepared in the previous step, and pyridinium chlorochromate (6.69 g, 31.0 mmol) in 600 ml of methylene chloride was stirred at room temperature for 1.5 hours. The reaction was poured onto 300 g of silica gel (230–400 mesh) and the material eluted with methylene chloride-ethyl acetate. Isolation of the major component gave 4.68 g (85%) of a green solid. Recrystallization of the solid from ethyl acetate gave N-benzyl-4-oxo-4-phenyl-butyramide as a white solid, mp 110–112° C.

Elemental Analysis for $C_{17}H_{17}NO_2$

Calc'd: C, 76.38; H, 6.41; N, 5.24.

Found: C, 76.33; H, 6.14; N, 5.26.

(C) Thiosemicarbazide (2.30 g, 25.2 mmol) was added to a solution of N-benzyl-4-oxo-4-phenyl-butyramide (4.12 g, 15.4 mmol), prepared in the previous step, in 100 ml of methanol plus 4.2 ml of 1 N HCl plus 4.2 ml of water and the reaction stirred at room temperature for 20 hours. The reaction was cooled in an ice bath and a white solid precipitated. The solid was collected by filtration and dried to give 4.61 g of a white solid. Recrystallization of the solid from ethyl acetate-methanol gave the title compound (2.05 g, 39%) as a white solid, mp 162–164° C.

Elemental Analysis for $C_{18}H_{20}N_4OS$

Calc'd: C, 63.50; H, 5.92; N, 16.46.

Found: C, 63.48; H, 5.77; N, 16.60.

EXAMPLE 5

4-[(Aminothioxomrethyl)-hydrazono]-N-methyl-4-phenylbutanamide (A) A solution of γ-phenyl-γ-butyrolactone (5.17 g, 31.9 mmol) in 40 ml of a 2 molar solution of methylamine in THF was stirred under nitrogen at room temperature for 23 hours. The solvent was removed under reduced pressure to give 6.15 g of a yellow solid. Recrystallization of the solid from ethyl acetate-hexane gave 4-hydroxy-N-methyl-4-phenyl-butyramide (4.81 g, 78%) as an off-white solid, mp 67–69° C.

Elemental Analysis for $C_{11}H_{15}NO_2$

Calc'd: C, 68.37; H, 7.82; N, 7.25.

Found: C, 68.60; H, 7.98; N, 7.32.

(B) A mixture of 4-hydroxy-N-methyl-4-phenyl-butyramide (4.50 g, 23.3 mmol), prepared in the previous step, and pyridinium chlorochromate (7.54 g, 35.0 mmol) in 200 ml of methylene chloride was stirred at room temperature for 2.5 hours. The reaction was poured onto 400 g of silica gel (230–400 mesh) and the material eluted with ethyl acetate-methylene chloride and then ethyl acetate. Isolation of the major component gave N-methyl-4-oxo-4-phenyl-butyramide (3.65 g, 82%) as an off-white solid, mp 80–82° C.

Elemental Analysis for $C_{11}H_{13}NO_2$

Calc'd: C, 69.09; H, 6.85; N, 7.32.

Found: C, 69.08; H, 6.87; N, 7.27.

(C) Thiosemicarbazide (2.60 g, 28.5 mmol) was added to a solution of N-methyl-4-oxo-4-phenyl-butyramide (3.33 g, 17.4 mmol), prepared in the previous step, in 60 ml of methanol plus 4.7 ml of 1 N HCl plus 4.7 ml of water and the reaction stirred at room temperature for 22 hours. The reaction was submerged in an ice bath and a solid precipitated. The solid was collected by filtration and dried to give 4.55 g of a white solid. The solid was triturated with water and then dried to give the title compound (4.10 g, 89%) as a white solid, mp 205–207° C.

Elemental Analysis for $C_{12}H_{16}N_4OS$

Calc'd: C, 54.52; H, 6.10; N, 21.19.

Found: C, 54.55; H, 6.02; N, 21.20.

EXAMPLE 6

4-[(Aminothioxomethyl)-hydrazono]-N-cyclohexyl-4-phenylbutanamide (A) A solution of γ-phenyl-γ-butyrolactone (5.16 g, 31.8 mmol) and cyclohexylamine (7.3 ml, 63.8 mmol) in 200 ml of benzene was refluxed under a nitrogen atmosphere for 3 days. The reaction was extracted with 1 N HCl, dried (MgSO₄) and the solvent removed under reduced pressure to give 7.07 g of a brown solid. Recrystallization of the solid from ethyl acetate-hexane gave N-cyclohexyl-4-hydroxy-4-phenyl-butyramide (4.22 g, 51%) as a white solid, mp 91–93° C.

Elemental Analysis for $C_{16}H_{23}NO_2$

Calc'd: C, 73.53; H, 8.87; N, 5.36.

Found: C, 73.48; H, 9.12; N, 5.48.

(B) A mixture of N-cyclohexyl-4-hydroxy-4-phenyl-butyramide (3.98 g, 15.2 mmol), prepared in the previous step, and pyridinium chlorochromate (4.94 g, 22.9 mmol) in 200 ml of methylene chloride was stirred at room temperature for 2.5 hours. The reaction was poured onto 400 g of silica gel (230–400 mesh) and the material eluted with methylene chloride-ethyl acetate. Isolation of the major component gave N-cyclohexyl-4-oxo4-phenyl-butyramide (3.28 g, 83%) as a light green solid, mp 109–111° C.

Elemental Analysis for $C_{16}H_{21}NO_2$

Calc'd: C, 74.10; H, 8.16; N, 5.40.

Found: C, 73.64; H, 8.11; N, 5.41.

(C) Thiosemicarbazide (1.75 g, 19.2 mmol) was added to a solution of N-cyclohexyl-4-oxo-4-phenyl-butyramide (3.30 g, 11.7 mmol), prepared in the previous step, in 40 ml of methanol plus 3.2 ml of 1 N HCl plus 3.2 ml of water and the reaction stirred at room temperature for 21 hours. The solid formed was removed by filtration and dried to give 2.69 g of a white solid. The filtrate was concentrated under reduced pressure to remove the methanol. The residue was partitioned between methylene chloride and water. The organic layer was separated, wash ed multiple times with water, dried ($MgSO_4$) and the solvent removed under reduced pressure to give 1.10 g of a white foam. The initial solid filtered from the reaction was dissolved in methylene chloride, washed multiple times with water, dried ($MgSO_4$) and the solvent removed under reduced pressure to give a white foam. Both materials were combined and crystallized from methylene chloride-ethyl acetate to give the title compound (3.31 g, 69%) as a white solid, mp 89–92° C.

Elemental Analysis for $C_{17}H_{24}N_4OS \cdot 0.9 \, C_4H_8O_2$

Calc'd: C, 60.09; H, 7.64; H; 13.61.

Found; C, 59.98; H, 7.67; N, 13.43.

EXAMPLE 7

4-[(Aminothioxomethyl)hydrazono]-N,N-dimethyl-4-phenylbutanamide (A) A solution of γ-phenyl-γ-butyrolactone (4.84 g, 29.8 mmol) in 200 ml of a 2 molar solution of dimethylamine in THF was stirred under a nitrogen atmosphere at room temperature for 2 days. The solvent was removed under reduced pressure to give 6.26 g of 4-hydroxy-N,N-dimethyl-4-phenyl-butyramide as a light brown oil, MS $[M+H]^+$ m/e 208.

Elemental Analysis for $C_{12}H_{17}NO_2$

Calc'd: C, 69.54; H, 8.27; N, 6.76.

Found: C, 68.13; H, 8.28; N, 6.65.

(B) In the same mariner as described in step (B) of Example 6,4-oxo-N,N-dimethyl-4-phenyl-butyramide (4.08 g, 72%) was obtained as an off-white solid, mp 56–58° C.

Elemental Analysis for $C_{12}H_{15}NO_2$

Calc'd: C, 70.22; H, 7.37; N, 6.82.

Found; C, 70.08; H, 7.40; N, 6.95.

(C) Thiosemicarbazide (2.75 g, 30.2 mmol) was added to a solution of 4-oxo-N,N-dimethyl-4-phenyl-butyramide (3.80 g, 18.5 mmol), prepared in the previous step, in 65 ml of methanol plus 5 ml of 1 N HCl plus 5 ml of water and the reaction stirred at room temperature for 28 hours. The solid present was collected by filtration to give4.76 g of a white solid. The solid was triturated with water and then dried to give the title compound (4.53 g, 88%) as a white solid, mp 173–175° C.

Elemental Analysis for $C_{13}H_{18}N_4OS$

Calc'd: C, 56.09; H, 6.52; N, 20.13.

Found: C, 55.64; H, 6.37; N, 19.78.

EXAMPLE 8

1-[4-[(Aminothioxomethyl)hydrazono]-1-oxo-4-phenylbutyl]piperidine (A) In the same manner as described in step (A) of Example 6, and replacing cyclohexylamine with piperidine, 4-hydroxy-4-phenyl-1-piperidin-1-yl-butan-1-one (4.86 g, 62%) was obtained as an off-white solid, mp 42–44° C.

Elemental Analysis for $C_{15}H_{21}NO_2$

Calc'd: C, 72.84; H, 8.56; N, 5.66.

Found: C, 72.83; H, 8.82; N, 5.63.

(B) A mixture of 4-hydroxy-4-phenyl-1-piperidin-1-yl-butan-1-one (4.00 g, 16.2 mmol), prepared in the previous step, and pyridinium chlorochromate (5.23 g, 24.3 mmol) in 150 ml of methylene chloride was stirred at room temperature for 2.25 hours. The reaction was poured onto 400 g of silica gel (230–400 mesh) and the material eluted with methylene chloride-ethyl acetate. Isolation of the major component gave 4-oxo-4-phenyl-1-piperidin-1-yl-butan-1-one (3.66 g, 92%) as a green solid. Recrystallization of a portion of this solid from ethyl acetate-hexane gave an analytically pure sample, mp 52–54° C.

Elemental Analysis for $C_{15}H_{19}NO_2$

Calc'd: C, 73.44; H, 7.81; N, 5.71.

Found: C, 73.55; H, 7.95; N, 5.70.

(C) In the same manner as described in step (C) of Example 7, the title compound (3.90 g, 91%) was obtained as a white solid, mp 181–183° C.

Elemental Analysis for $C_{16}H_{22}N_4OS$

Calc'd: C, 60.35; H, 6.96; N, 17.59.

Found: C, 60.14; H, 7.06; N, 17.58.

EXAMPLE 9

4-[(Aminothioxomethyl)-hydrazono]-N-(1,5-dimethylhexyl)-4-phenyl-butanamide (A) A solution of γ-phenyl-γ-butyrolactone (5.02 g, 30.9 mmol) and 1,5-dimethylhexylamine (10.4 ml, 61.7 mmol) in 200 ml of benzene was refluxed under a nitrogen atmosphere for 40 hours. An additional 10.4 ml (61.7 mmol) of 1,5-dimethylhexylamine was added and the reaction refluxed for 26 hours. The reaction was extracted with 1 N HCl, dried ($MgSO_4$) and the solvent removed under reduced pressure to give to give 8.26 g of a light brown solid. Recrystallization of the solid from ethyl acetate-hexane gave N-(1,5-dimethyl-hexyl)-4-hydroxy-4-phenyl-butyramide (3.72 g, 41%) as a white solid, mp 72–89° C.

Elemental Analysis for $C_{18}H_{29}NO_2$

Calc'd: C, 74.18; H, 10.03; N, 4.81.

Found: C, 74.50; H, 10.34; N, 4.79.

(B) A mixture of N-(1,5-dimethyl-hexyl)-4-hydroxy-4-phenyl-butyramide (3.50 g, 12.0 mmol), prepared in the previous step, and pyridinium chlorochromate (3.89 g, 18.0 mmol) in 150 ml of methylene chloride was stirred at room temperature for 1.25 hours. The reaction was poured onto 400 g of silica gel (230–400 mesh) and the material eluted with methylene chloride-ethyl acetate. Isolation of the major component gave N-(1,5-dimethyl-hexyl)-4-oxo-4-phenyl-butyramide (2.71 g, 78%) as a light green solid, mp 84–87° C.

Elemental Analysis for $C_{18}H_{27}NO_2$

Calc'd: C, 74.70; H, 9.40; N, 4.84.

Found: C, 74.38; H, 9.65; N, 4.89.

(C) Thiosemicarbazide (1.32 g, 14.5 mmol) was added to a solution of N-(1,5-dimethyl-hexyl)-4-oxo-4-phenyl-butyramide (2.54 g, 87.9 mmol), prepared in the previous step, in 30 ml of methanol plus 2.4 ml of 1 N HCl plus 2.4 ml of water and the reaction stirred at room temperature for 48 hours. The reaction was concentrated under reduced pressure to remove the methanol. The residue was partitioned between methylene chloride and water. The organic layer was separated, washed multiple times with water, dried ($MgSO_4$) and the solvent removed under reduced pressure to give 2.95 g of an off-white solid foam. Purification of this foam by chromatography on silica gel (230–400 mesh) using 3:1 hexane-ethyl acetate and then 3:1 ethyl acetate-methylene chloride as the eluents gave the title compound (2.63 g, 82%) as a white foam, mp 58–65° C.

Elemental Analysis for $C_{19}H_{30}N_4OS$

Calc'd: C, 62.95; H, 8.34; N, 15.45.

Found: C, 62.53; H, 8.47; N, 15.35.

Pharmacology

In Vivo Assa.: Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Procedure No. 352, modified for use with ninety-six well microtiter plates. After reconstitution with water the reagent contains 300 U/I cholesterol oxidase, 100 U/I horse radish peroxidase, 0.3 mmoles/l of 4-aminoantipyrine and 30.0 mmoles/l of p-hydroxybenzenesulfonate in a pH 6.5 buffer. In the reaction cholesterol is ;oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 μl of serum is injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the per cent of total absorbance. HDL cholesterol concentration, in serum, is calculated as the per cent of total cholesterol as determined by FPLC multiplied by the total serum cholesterol concentration.

TABLE I

Cholesterol Fed Rat

| Example | % Increase in HDL (Dose) |
|---|---|
| Example 1 | 56% (100 mg/kg) |
| Example 2 | 61.7% (100 mg/kg) |
| Example 3 | 36.4% (50 mg/kg) |
| Example 4 | 49.5% (50 mg/kg) |
| Example 5 | 43.3% (100 mg/kg) |
| Example 6 | 28.1% (82 mg/kg) |
| Example 7 | 56.2% (50 mg/kg) |
| Example 8 | 52.8% (50 mg/kg) |
| Example 9 | 40.4% (50 mg/kg) |

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties In suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partrially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to realease the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from high density lipoprotein insufficiency must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral or parenteral administration will be determined by the administering physician based on experience with the individual subject treated and standard medical principles.

Preferably the pharmaceutical composition is in unit dosage form, e.g., as tablets or capsules. In such form, the composition is sub-divided in unit doses containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. A compound according to the formula:

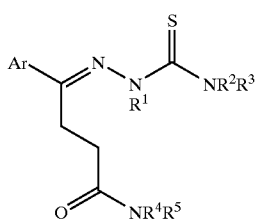

A wherein:

$R^1$, $R^2$, and $R^3$ are independently hydrogen, $C_1$–$C_6$ alkyl, phenyl or —$(CH_2)_{1-6}$ phenyl where phenyl is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_{10}$ alkyl, $C_3$–$C_8$ cycloalkyl, —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH, or $R^4$ and $R^5$ together with the nitrogen to which $R^4$ and $R^5$ are attached form a ring containing 4–7 carbon atoms;

and Ar is phenyl, naphthyl, furanyl, pyridinyl or thenyl which may be optionally substituted by halogen, cyano, nitro, $C_1$–$C_6$ alkyl, $C_3$–$C_6$ cycloalkyl, phenyl, $C_1$–$C_6$ alkoxy, phenoxy, trifluoromethyl, $C_1$–$C_6$ alkoxycarbonyl, —$CO_2H$ or OH;

with the proviso that Ar and $R^2$ cannot simultaneously be optionally substituted phenyl when the $R^1$ and $R^3$ are independently hydrogen or alkyl.

2. A compound according to claim 1 which is selected from the group consisting of 2-(4-butylamino-4-oxo-1-phenyl-butylidene)-hydrazinothiocarboxamide, 4-[(aminothioxomethyl)hydrazono]-N-(1-methylethyl)-4-phenyl-butanamide, 4-[(aminothioxomethyl)-hydrazono]-4-phenylbutanamide, 4-[(aminothioxomethyl)-hydrazono]-N-benzyl-4-phenylbutanamide, 4-[(aminothioxomethyl)-hydrazono]-N-methyl-4-phenylbutanamide, 4-[(aminothioxomethyl)-hydrazono]-N-cyclohexyl-4-phenylbutanamide, 4-[(aminothioxomethyl)hydrazono]-N,N-dimethyl-4-phenylbutanamide, 1-[4-[(aminothioxomiethyl)hydrazono]-1-oxo-4-phenylbutyl]piperidine, and 4-[(aminothioxomethyl)-hydrazono]-N-(1,5-dimethylhexyl)-4-phenyl-butanamide.

3. A pharmaceutical composition for the treatment of atherosclerosis which comprises a pharmaceutically acceptable carrier and a therapeutically effective amount of a compound according to the formula:

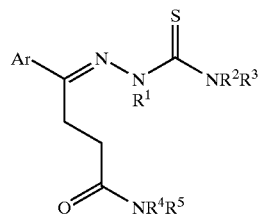

A wherein:

$R^1$, $R^2$, and $R^3$ are independently hydrogen, $C_1$–$C_6$ alkyl, phenyl or —$(CH_2)_{1-6}$ phenyl where phenyl is optionally substituted by halogen, cyano, nitro, $C_1$–$C_6$ alkyl, $C_1$–$C_6$ alkoxy, trifluoromethyl, $C_1$–$C_6$ alkoxycarbonyl, —$CO_2H$ or OH;

$R^4$ and $R^5$ are independently hydrogen, $C_1$–$C_{10}$ alkyl, $C_3$–$C_8$ cycloalkyl, —$(CH_2)_{0-6}Ar^1$ where $Ar^1$ is phenyl, naphthyl, furanyl, pyridinyl or thenyl and $Ar^1$ can be optionally substituted by halogen, cyano, nitro, $C_1$–$C_6$ alkyl, phenyl, $C_1$–$C_6$ alkoxy, phenoxy, trifluoromethyl, $C_1$–$C_6$ alkoxycarbonyl, —$CO_2H$ or OH, or $R^4$ and $R^5$ together with the nitrogen to which $R^4$ and $R^5$ are attached form a ring containing 4–7 carbon atoms;

and Ar is phenyl, naphthyl, furanyl, pyridinyl or thienyl which may be optionally substituted by halogen, cyano, nitro, $C_1$–$C_6$ alkyl, $C_3$–$C_6$ cycloalkyl phenyl, $C_1$–$C_6$ alkoxy, phenoxy, trifluoromethyl, $C_1$–$C_6$ alkoxycarbonyl, —$CO_2H$ or OH.

4. A pharmaceutical composition according to claim 3 wherein the compound used is selected from the group consisting of:

2-(4-butylamino-4-oxo-1-phenyl-butylidene)-hydrazinothiocarboxamide,

4-[(aminothioxomethyl)hydrazono]-N-(1-methylethyl)-4-phenyl-butanamide,

4-[(amninothioxomethyl)-hydrazono]-4-phenylbutanamide,

4-[(aminothioxomethyl)-hydrazono]-N-benzyl-4-phenylbutanamide,

4-[(aminothioxomethyl)-hydrazono]-N-methyl-4-phenylbutanamide,

4-[(aminothioxomethyl)-hydrazono]-N-cyclohexyl-4-phenylbutanamide,

4-[(aminothioxomethyl)hydrazono]-N,N-dimethyl-4-phenylbutanamide,

1-[4-[(aminothioxomnethyl)hydrazono]-1-oxo4-phenylbutyl]piperidine, and

4-[(aminothioxomethyl)-hydrazono]-N-(1,5-dimethylhexyl)-4-phenyl-butanamide.

\* \* \* \* \*